(12) United States Patent
Brown et al.

(10) Patent No.: US 8,995,617 B2
(45) Date of Patent: Mar. 31, 2015

(54) RADIOTHERAPEUTIC APPARATUS

(75) Inventors: Kevin Brown, Horsham (GB); Adrian Maxwell Smith, London (GB)

(73) Assignee: Elekta AB (publ), Stockholm (SE)

( * ) Notice: Subject to any disclaimer, the term of this patent is extended or adjusted under 35 U.S.C. 154(b) by 356 days.

(21) Appl. No.: 13/503,478

(22) PCT Filed: Oct. 1, 2010

(86) PCT No.: PCT/EP2010/005988

§ 371 (c)(1),
(2), (4) Date: Apr. 23, 2012

(87) PCT Pub. No.: WO2011/050887

PCT Pub. Date: May 5, 2011

(65) Prior Publication Data

US 2012/0215051 A1    Aug. 23, 2012

(30) Foreign Application Priority Data

Oct. 26, 2009  (WO) .................. PCT/EP2009/007641
Sep. 2, 2010   (WO) .................. PCT/EP2010/005373

(51) Int. Cl.
   *A61N 5/10*   (2006.01)

(52) U.S. Cl.
   CPC ............ *A61N 5/1042* (2013.01); *A61N 5/1047* (2013.01)
   USPC ......................................................... 378/65

(58) Field of Classification Search
   CPC .  A61N 5/1042; A61N 5/1043; A61N 5/1044; A61N 5/1045; A61N 5/1047
   USPC ................................................... 378/64, 65
   See application file for complete search history.

(56) References Cited

U.S. PATENT DOCUMENTS 6,411,093 B2 *  6/2002  Schwilch et al. .............. 324/322
6,587,242 B1 *  7/2003  Shake et al. .................... 398/98

(Continued)

FOREIGN PATENT DOCUMENTS

WO    WO 2007124760 A1   11/2007  ............... A61N 5/10

OTHER PUBLICATIONS

Cedric X. Yu, "Intensity-modulated arc therapy with dynamic multileaf collimation: an alternative to tomotherapy," Phys. Med. Biol. 40 (1995), 1435-1449.*

(Continued)

*Primary Examiner* — Allen C. Ho
(74) *Attorney, Agent, or Firm* — Sunstein Kann Murphy & Timbers LLP (57) ABSTRACT

The ability to provide a fine resolution variation in the dose rate of radiotherapeutic apparatus would allow delivery times of Volumetric Modulated Arc Therapy (VMAT) and related techniques to be reduced significantly. A radiotherapeutic apparatus is described, comprising a source of radiation able to issue pulses of radiation at a base frequency, and a control apparatus arranged to permit pulses provided these match a pulse pattern chosen to achieve a selected time-averaged power level, the chosen pulse pattern being one selected from a plurality of pulse patterns that include patterns consisting of trains of pulses that include, relative to the base frequency, at least every nth and every $m^{th}$ pulse where $n \neq m$ and the $n^{th}$ and $m^{th}$ pulses are non-coincident. Essentially, such an apparatus issues a pulse if it is the nth or the $m^{th}$ or the $k^{th}$ (etc) where n, m, k . . . are selectable independently.

20 Claims, 5 Drawing Sheets

(56) References Cited

U.S. PATENT DOCUMENTS

| | | | |
|---|---|---|---|
| 7,961,843 B2* | 6/2011 | Brown et al. .................. | 378/65 |
| 2008/0144772 A1 | 6/2008 | Yi et al. ......................... | 378/65 |
| 2009/0121155 A1 | 5/2009 | Brown et al. .............. | 250/492.1 |
| 2009/0154650 A1 | 6/2009 | Tanabe ......................... | 378/137 |

OTHER PUBLICATIONS

International Search Report and Written Opinion, PCT/EP2010/005988, date of mailing Feb. 18, 2011, 13 pages.

* cited by examiner

RADIOTHERAPEUTIC APPARATUS

FIELD OF THE INVENTION

The present invention relates to radiotherapeutic apparatus.

BACKGROUND ART

Traditionally, in static conformal radiation therapies the dose rate was relatively unimportant, and accelerator designs tended to work with a fixed Pulse Repetition Frequency (PRF) at which the RF source was pulsed in order to create radiation pulses. To vary the rate at which dose was imparted to the patient, the base frequency could be halved, repeatedly if necessary. Thus, the apparatus generated fixed dose rates at fixed divisors e.g. ½, ¼, ... of the maximum output power, corresponding to like fractions of the base frequency.

This design approach was employed on accelerators because these systems were originally designed with power supplies that were susceptible to the AC effect of the mains voltage. In particular the High Voltage of the Modulator used to pulse the Magnetron would have a ripple at the frequency of the mains supply, and this ripple directly coupled through the Magnetron into the frequency of the RF and then to a ripple on the dose rate. This effect could be avoided by ensuring that the Modulator was always pulsed at a fixed position relative to the incoming AC supply. Hence, a 400 Hz pulse rate would be suitable for a 50 Hz supply. Modern accelerator systems typically use switched mode power supplies which are not susceptible to the mains AC and therefore are not constrained in this way.

This approach imposes limitations when the apparatus is used in modern Volumetric Modulated Arc Therapy (VMAT) therapies, such as we describe in our WO2007/124760. In these dynamic techniques, the dose rate is used as a variable in order to match the maximum speed of the moving machine axes and therefore create the specified dose, expressed as mu/mm or mu/.degree. Thus, when the optimising algorithm comes to calculate the ideal dose rate for a portion of the treatment, it has only a very ILO limited set of dose rates to choose from. This leads to situations where the optimising algorithm is forced to select a dose rate that can be almost half the optimal dose rate, because of the simple PRF divisors used. The end result of this is longer treatment times.

This limitation also causes step changes in other machine parameters, such as the gantry speeds and leaf speeds. This causes a reduction in delivery accuracy, because the servo systems must compensate for gross changes in demand.

SUMMARY OF THE INVENTION

If it were possible to achieve a fine resolution variation in the dose rate, then delivery times of VMAT and related or similar techniques would be significantly reduced. In theory, an improvement of up to double the speed and improved conformance to plan of the delivered dose could be obtained, because the machine servos would be more able to smoothly track the desired delivery.

The present invention therefore provides a radiotherapeutic apparatus comprising a source of radiation able to issue pulses of radiation at a base frequency, and a control apparatus arranged to permit pulses according to a pulse pattern chosen to achieve a selected time-averaged power level, the chosen pulse pattern being one selected from a plurality of pulse patterns, the plurality of pulse patterns including at least one pulse pattern consisting of a train of pulses that includes, relative to the base frequency, at least every $n^{th}$ and every $m^{th}$ pulse where $n \neq m$ and the $n^{th}$ and $m^{th}$ pulses are non-coincident.

The use of a 'base frequency' is a way of describing that there is typically a minimum gap between any two pulses which is required to allow the pulse power system to get ready for the next pulse. Therefore the base frequency is a mechanism to enforce that the pulses do not violate this minimum gap.

Essentially, such an apparatus issues a pulse if it is the $n^{th}$ or the $m^{th}$ or the $k^{th}$ (etc) where both the values of the repetition rates n, m, k . . . and the number of repetitions are selectable independently. So in the above example, the odd pulses, every $4^{th}$, and every $8^{th}$ pulse are included in order to give a $\frac{7}{8}^{ths}$ output. This is easier if n and m are powers of 2, but this is not strictly necessary.

The pulse pattern can be obtained by selecting an integer representing the desired power level, and then inserting an $n^{th}$ pulse if the binary number representing the integer has a 1 digit at the $(q+1)^{th}$ position from left to right where q is the $n^{th}$ digit of the binary carry sequence. The binary carry sequence is defined at mathworld.wolfram.com/BinaryCarrySequence.html as the sequence a(n) given by the exponents of the highest power of 2 dividing n, i.e., the number of trailing 0s in the binary representation of n. For n=1, 2, 3, . . . , the first few numbers of the sequence are 0, 1, 0, 2, 0, 1, 0, 3, 0, 1, 0, 2 and so on.

Alternatively, the pulse pattern can be obtained by combining selected streams from a collection of 'i' different pulse streams, being a stream carrying every $2^1$nd pulse, a stream carrying every $2^2$th pulse, a stream carrying every $2^3$th pulse, etc up to a stream carrying every $2^i$th pulse (relative to a base frequency). By phasing the streams so that each stream consists of pulses that are non-coincident with pulses from other streams, a suitable pattern of pulses can be created. Controlling which streams are included then allows any one of $2^i$ power levels to be chosen.

Generally speaking, the control apparatus will then comprise a generator for a plurality of signals at frequencies below that of the base frequency, each of which is selectable independently, and an OR operator combining the selected signals. The plurality of signals preferably have frequencies that are $\frac{1}{2}^k$th of the base frequency where k is an integer and is different for each signal. Each signal is also preferably offset from a pulse of the base frequency by $2^{(k-1)}$ pulses.

For ease of engineering, the control apparatus can be a memory in which a table is retained, the table containing the sequence of pulses to be issued. The table can be freshly populated with a sequence when a power level is selected, by computing a sequence and loading this into the table. Alternatively, the table can contain sequences for a plurality of (preferably all the) power levels and the control unit can be adapted to select a desired sequence. Additionally (or alternatively) the control apparatus may be implemented in digital logic to implement the shift and decode operations necessary to implement the patterns.

Alternatively, pulsed signals as described above can be activated or de-activated as required, and an output derived by applying an OR operation to the pulse trains.

The above is made both conceptually and practically easier if the available values of n are of the form $n=2^p$ where p is a positive integer, ideally between 6 and 10. In the following discussion, this will be the case for all examples. It should be borne in mind, however, that this is not essential and other formats could advantageously be adopted. Where $n \neq 2^p$, then either the highest or lowest 'n' levels of a pattern of 'm' levels can be used (where $m=2^p$), or 'n' levels can be selected from the 'm' available levels to create a subset of 'n' levels.

Another way of looking at the invention is by considering the pulses that are suppressed, rather than the pulses that are included. Accordingly, the present invention also provides a radiotherapeutic apparatus comprising a source of radiation able to issue pulses of radiation at a base frequency, and a control apparatus in which are defined a plurality of pulse patterns each of which are independently controllable between a "suppress" state and an "active" state and each of which controls every $n^{th}$ pulse, n being different for each pattern, wherein the control apparatus is arranged to suppress a pulse if a pattern in a "suppress" state controls that pulse, and that pulse is not controlled by a pattern with a higher value of n that is in an "active" state.

Thus, for example, by removing every $8^{th}$ pulse, a power output of $7/8^{ths}$ of full power is obtained, which is not possible through simple frequency division. This can then be further fine-tuned by adding back in every $32^{nd}$ pulse, slightly raising the power level to $29/32$nds. In this example, a pulse will be omitted if it is one of the pulses in the "every $8^{th}$ pulse" pattern unless it is also one of the pulses in the "every $32^{nd}$ pulse" pattern. Such a pulse would be controlled by the higher-n "every $32^{nd}$ pulse" pattern instead of the "every $8^{th}$ pulse" pattern.

By use of the invention as defined above, we move from rigid factors of 1×, ½×, ¼× and ⅛× etc and allow the apparatus to select from any desired number of smoothly distributed of power levels between zero and 100%. The number of discrete power levels can be chosen to be sufficiently high that it is effectively continuous for all practical purposes.

In this application, we refer interchangeably to the output power level of the apparatus, and the dose rate that is delivered to the patient. The pulses produced by the apparatus essentially represent a mean power level in the magnetron, which is converted to an RF output into the linear accelerator, which is converted to a radiation dose. The output power level and the dose rate are therefore equivalent terms insofar as this invention is concerned.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
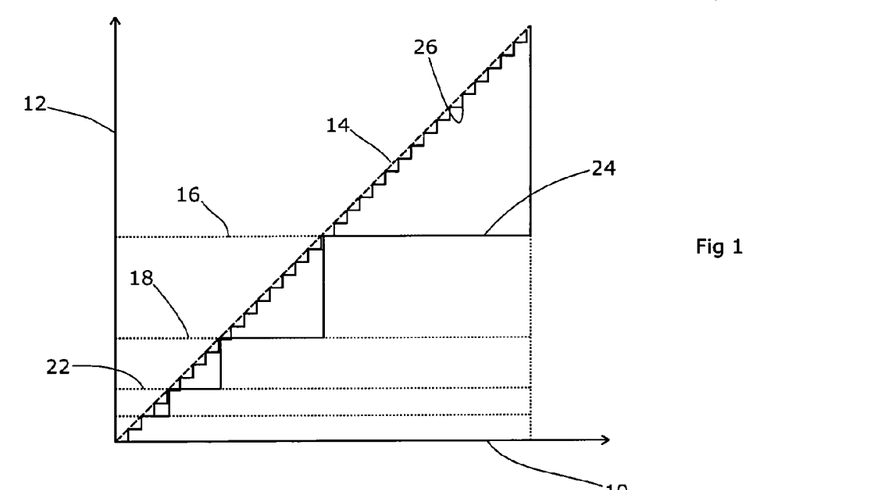
FIG. 1 illustrates the variable output powers available.

FIG. 1 illustrates the problem addressed by the present invention. It plots the desired output power along the x axis 10 versus the actually obtained output power along the y axis 12. The ideal behaviour would of course be a 1:1 straight line as illustrated at 14. However, known systems are far less linear than this. As the only available power levels are full power, ½ power 16, ¼ power 18 and ⅛ power 22 (etc), and as it is important not to overdose a patient, if the desired power is between one of these levels then the lower level must be adopted and the treatment time extended correspondingly (or another form of compensation applied). This results in behaviour according to the line 24, which (unsurprisingly) becomes very non-linear at higher power levels.

The present invention smoothes this behaviour by allowing the selection of intermediate fractions of the maximum power level. Thus, instead of being limited to fractions of $1/2^i$, it permits the adoption of any level $n/2^i$ (where n and i are positive integers and $n \le 2^i$). This results in the distinctly smoother plot 26, in which the only limitation to the smoothness is the value of i; as i increases, the plot becomes smoother.

If, for some reason, a number of power levels needs to be provided which is not an integer power of 2, then the necessary number can be selected from the next higher integer power of 2. However, this offers no particular benefits that we can see, and therefore the examples which follow will all provide a number of power levels that is an integer power of 2.

Figure 2A:
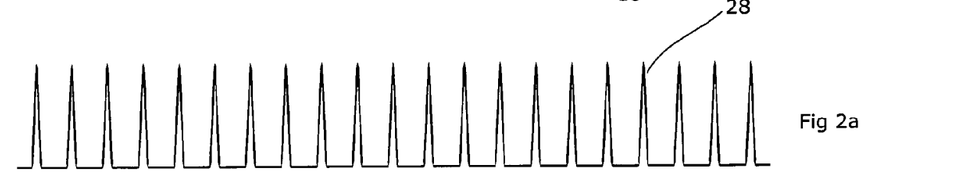
FIGS. 2a to 2c illustrate known forms of pulsed output.
Figure 2B:
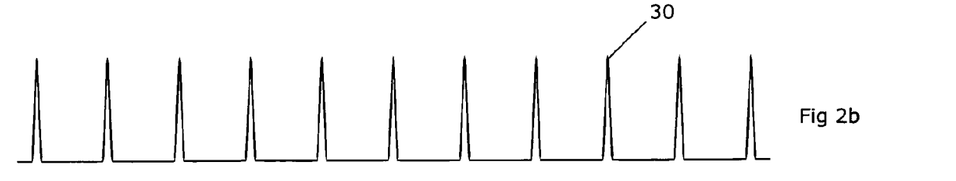
Figure 2C:
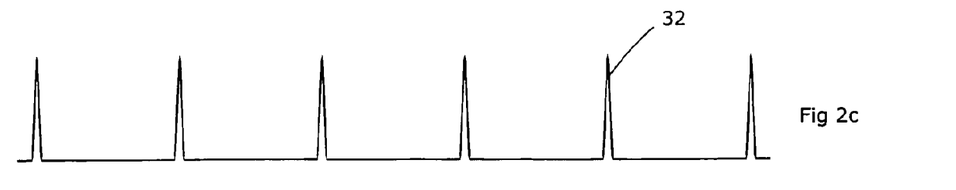

FIGS. 2a to 2c show the effect of FIG. 1 on the actual output power of a known device. FIG. 2a shows the output at maximum power; this consists of a stream of output pulses 28 spaced according to the base frequency. It should be noted that for reasons of clarity the pulses are shown with an exaggerated width relative to the spacing between them; in practice the pulses have a width about 3 orders of magnitude less than their time separation, typically a 2.5 microsecond pulse every 2.5 milliseconds. FIG. 2b shows the selection of ½ power, resulting in the omission of every other pulse. The time-averaged power of the remaining pulses 30 is therefore half that of the pulses 28. As the pulse rate is very high (typically 400-500 Hz) it is the average over many pulses that matters. FIG. 2c shows a further frequency division, to ¼ power, leaving only every fourth pulse 32 from the pulse train 28 of FIG. 2a.

Figure 3:
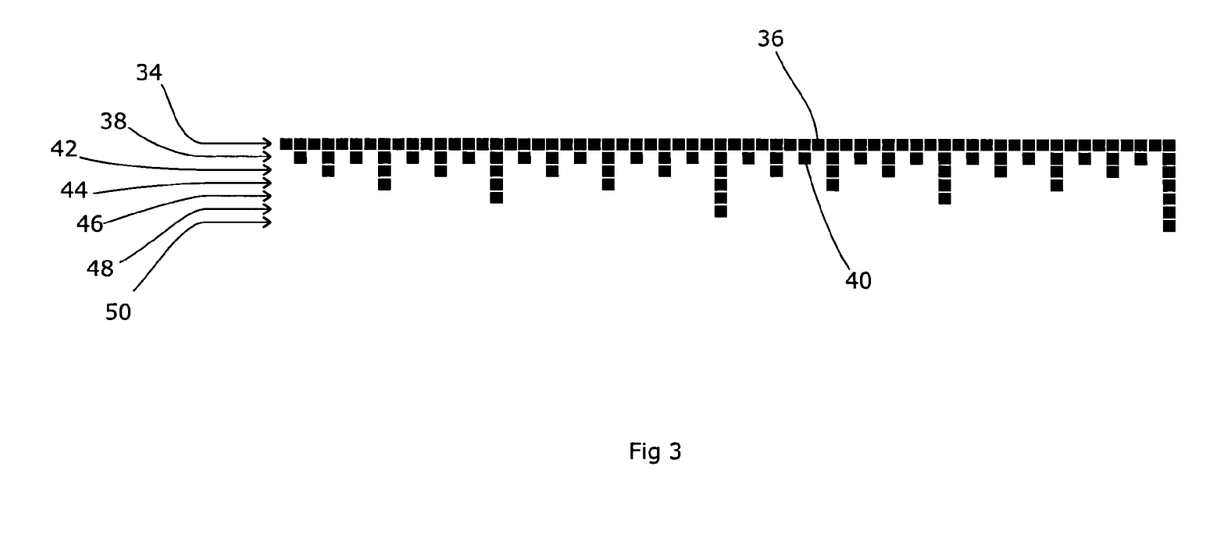
FIG. 3 illustrates the pulsed outputs of FIG. 2 schematically.

FIG. 3 shows a graphical representation of the frequency division shown in FIGS. 2a to 2c. A horizontal line 34 of adjacent blocks 36 denotes a steady stream of pulses at the base frequency, i.e. full power. The next line 38 below line 34 denotes the next lower power level, and consists of a stream of pulses 40 which omits every other pulse. Likewise, line 42 illustrates the next lower power level, in which one pulse in 4 remains. Line 44 shows one pulse in 8, and lines 46, 48 and 50 show one pulse in 16, 32 and 64 respectively.

The present invention employs a technique known as "Bit Rate Multiplying" to maintain all the design criteria discussed above (and the benefits thereof) while achieving a higher resolution of PRF variation and therefore dose rates.

There are, essentially, two ways to view the present invention, which have corresponding ways in which the invention can be engineered. The stream of pulses in the desired output pulse stream differs from the stream of pulses at the base frequency in that some pulses are absent from the output stream. The output stream can thus be characterised by the pulses that are absent, or by the pulses that are present. This corresponds to an engineering choice between suppressing pulses, or permitting them.

From the approach of suppressing pulses, the invention requires the suppression of pulses according to a number of patterns. Each pattern suppresses every $n^{th}$ pulse that is not controlled by a pattern with a higher value of n, where n is unique to that pattern and is a power of 2 (including $n=2^0$).

To achieve the full range of power levels, a user can then be allowed to select any, some or all of the individual suppression patterns, in any combination. The effect of this is shown by way of example in FIG. 4, in the form of a modulo 64 pattern (therefore offering 64 power levels). This is set out in the same manner as FIG. 3.

Figure 4:
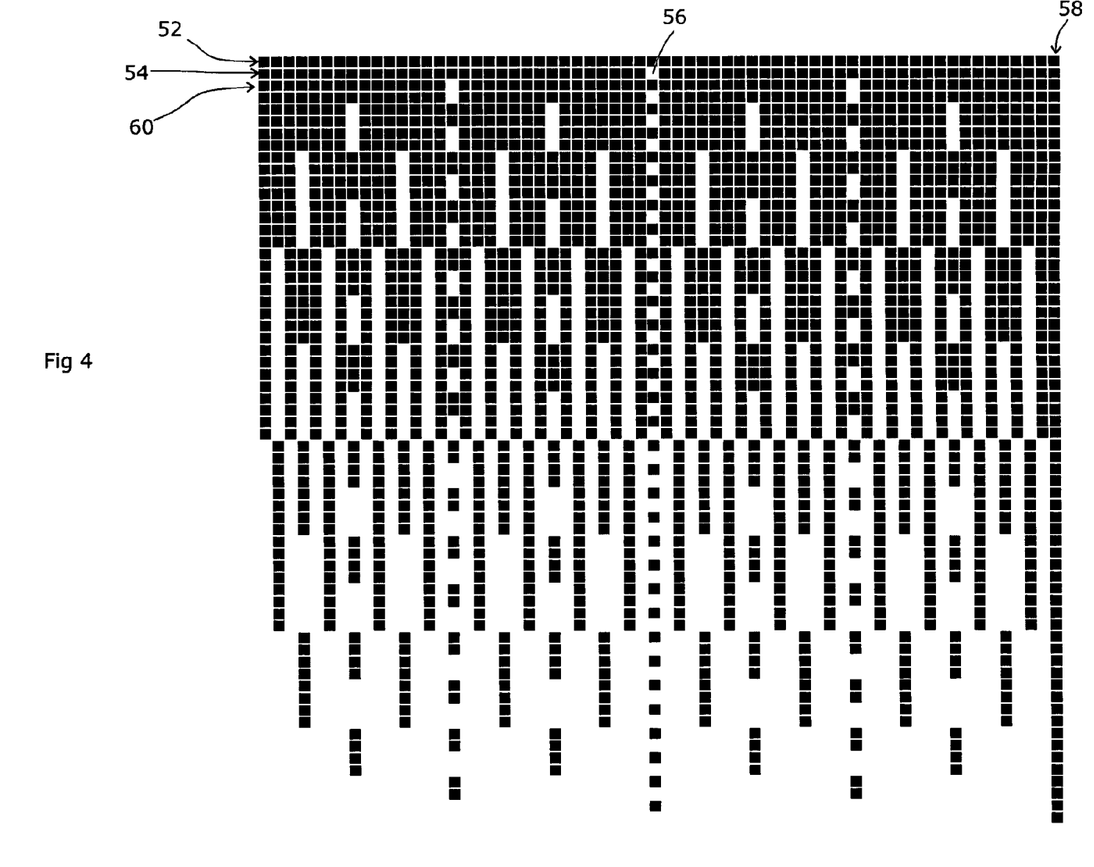
FIG. 4 illustrates the pulsed outputs of the present invention graphically.

At the highest power level 52, all pulses are present and no pulses from the base frequency are suppressed. The device is therefore operating at full power.

At the next highest power level 54, one pulse 56 out of every 64 pulses is omitted. This therefore corresponds to a time-averaged power level of $63/64^{ths}$ or about 98%. This power level could correspond to selecting a "one in 64" pattern, but for continuity with the other power levels is best regarded as being the selection of a "one in 32" pattern together with the non-selection of a "one in 64" pattern. Thus, the $64^{th}$ pulse 58 remains in place as, although it is the $32^{nd}$ pulse after the omitted $32^{nd}$ pulse 56, it is controlled by a higher pattern.

The power level immediately below the $63/64^{ths}$ level, i.e. the $62/64^{ths}$ power level 60 is then obtained by selecting just the "one in 16" pattern. This suppresses the 16.sup.th and the $48^{th}$ pulse, but leaves the $32^{nd}$ and $64^{th}$ pulses in place as these are controlled by patterns with a higher value of n—i.e. the "one in 32" and "one in 64" patterns. The result is that only two pulses in every 64 are omitted, giving 62 pulses out of a possible 64.

A power level of $61/64^{ths}$ can then be obtained by selecting both the "one in 32" pattern and also the "one in 16" pattern. This omits the $16^{th}$, $32^{nd}$ and $48^{th}$ pulses, leaving the $64^{th}$ pulse 58 present.

The sequence can then continue, selecting and deselecting patterns as necessary to achieve a specific power level. The application of these simple (and hence easily computable) rules allows the selection of any of $2^t$ evenly spaced power levels. The resulting pulse patterns are generally evenly spaced, retaining the necessary thermal stability. The base frequency is retained, and the patterns of omitted pulses are deterministic and predictable. Thus, all the necessary advantages of the prior system are retained but the power levels are spread evenly.

The desired power level can in fact be chosen as a binary number—for the above 64-level (6-bit) system this will be between 000000 and 111111. The value chosen for these bits then configures the output pulse pattern; each pattern is controlled by one bit. Thus, if the leftmost (most-significant) bit (MSB) is active (a "1" value) then the $2^0$ pattern is activated. Likewise, if the right-most (least-significant) bit (LSB) is active then the $2^5$ pattern is activated, in this case. If a higher resolution pattern were adopted, such as a modulo-256 pattern, then the binary power level would be between 00000000 and 11111111 and the LSB would correspond to a $2^7$ pattern.

In practice, radiotherapeutic apparatus uses a Pulse Repetition Frequency (PRF) timing generator to create RF trigger pulses and related signals that drive the creation of an output pulse. The design of the PRF timing generator will therefore use this pattern to blank selected RF trigger pulses (etc) and therefore blank (or suppress) the creation of a radiation pulse. In effect the white areas in the pattern indicate the absence of an RF pulse and therefore the absence of a radiation pulse.

This technique produces an optimal pattern. When this pattern is used to blank the PRF timing generator, it can replicate the previous known divisors (½, ¼ etc) but in between these there is a set of deterministic, optimally spaced pulse patterns which create a set of finer pulse repetition frequencies.

As noted above, this technique therefore a) continues to allow the electron gun current to be synchronised with the pulse repetition frequency as above.

b) Allows the selection of dose rates to a finer resolution in addition to the classic ½, ¼, . . . divisors.

c) Produces a pulse pattern that continues to offer the benefits of thermal equilibrium by optimally spacing the pulses in the time domain.

d) Produces a deterministic pattern that allows the prediction of the pulse position given a single number m and a reference pulse. This enables synchronised imaging schemes to continue to work.

The PRF timing generator can decide whether to allow a particular pulse by running the relevant algorithm, using appropriate digital logic to produce the sequence as per the algorithm in real time and output a control signal that is used to produce or suppress individual pulses. If this approach is considered too computationally intensive, then an alternative solution may be to calculate the results of the algorithm when the power level is set and store the results in a lookup table which the PRF timing generator can consult for each pulse. Alternatively, the lookup table could include the patterns for all available power levels, and the PRF timing generator could consult the appropriate part of the table, such as one specific line corresponding to the chosen power level.

As noted above, another way of looking at the invention is by considering the pulses that are included, rather than the pulses that are suppressed. In this case, the relevant rule is that the pulse pattern is one that consists of at least one train of pulses that include, relative to the base frequency, at least every $n^{th}$ pulse. Multiple such trains can be superimposed, i.e. also including every $m^{th}$ pulse and/or every $k^{th}$ pulse (etc), where $n \neq m \neq k$.

Essentially, such an apparatus issues a pulse if it is the $n^{th}$ or the $m^{th}$ or the $k^{th}$ (etc) where both the values of the repetition rates n, m, k . . . and the number of repetitions are selectable independently. So, for example, the odd pulses, every $4^{th}$, and every $8^{th}$ pulse can be included in order to give a $7/8^{ths}$ output.

One way of deriving a suitable pattern is to use the "Binary Carry Sequence", a known numerical sequence that is defined (for example) at mathworld.wolfram.com/BinaryCarrySequence.html as the sequence a(n) given by the exponents of the highest power of 2 dividing n, i.e., the number of trailing 0s in a binary representation of n. For n=1, 2, 3, 4, . . . , the first few numbers of the sequence are 0, 1, 0, 2, 0, 1, 0, 3, 0, 1, 0, 2 and so on. The binary carry sequence can be repeated modulo the number of possible output power levels. Thus, in a system having 8 power levels the sequence would be 0, 1, 0, 2, 0, 1, 0, 3, and then repeating.

The pulse pattern can be obtained by resolving the selected power level as an integer (which will therefore be representable as a binary number), and then inserting an $n^{th}$ pulse if the binary number has a 1 digit at the $(q+1)^{th}$ position reading from left to right, where q is the $n^{th}$ digit of the binary carry sequence.

Thus, if we assume that 64 power levels are to be provided, then each power level can be numbered 0 to 63, or 000000 to 111111 in binary. If power level 53 is selected (as an example) this is 110101 in binary. For 64 power levels, the complete binary carry sequence is:

| | |
|---|---|
| 1 | 0 |
| 2 | 1 |
| 3 | 0 |
| 4 | 2 |
| 5 | 0 |
| 6 | 1 |
| 7 | 0 |

| | |
|---|---|
| 8 | 3 |
| 9 | 0 |
| 10 | 1 |
| 11 | 0 |
| 12 | 2 |
| 13 | 0 |
| 14 | 1 |
| 15 | 0 |
| 16 | 4 |
| 17 | 0 |
| 18 | 1 |
| 19 | 0 |
| 20 | 2 |
| 21 | 0 |
| 22 | 1 |
| 23 | 0 |
| 24 | 3 |
| 25 | 0 |
| 26 | 1 |
| 27 | 0 |
| 28 | 2 |
| 29 | 0 |
| 30 | 1 |
| 31 | 0 |
| 32 | 5 |
| 33 | 0 |
| 34 | 1 |
| 35 | 0 |
| 36 | 2 |
| 37 | 0 |
| 38 | 1 |
| 39 | 0 |
| 40 | 3 |
| 41 | 0 |
| 42 | 1 |
| 43 | 0 |
| 44 | 2 |
| 45 | 0 |
| 46 | 1 |
| 47 | 0 |
| 48 | 4 |
| 49 | 0 |
| 50 | 1 |
| 51 | 0 |
| 52 | 2 |
| 53 | 0 |
| 54 | 1 |
| 55 | 0 |
| 56 | 3 |
| 57 | 0 |
| 58 | 1 |
| 59 | 0 |
| 60 | 2 |
| 61 | 0 |
| 62 | 1 |
| 63 | 0 |
| 64 | 6 |

With this information, the pulse pattern can be derived easily. For the first pulse (i.e. n=1), the first digit of the binary carry sequence is 0. The chosen power level (53) is 110101 which has a "1" at the leftmost position. Therefore, the first pulse from the base frequency signal is inserted or otherwise included.

For the second pulse, n=2 and the second digit of the binary carry sequence is 1. The binary number 110101 has a "1" at the 2nd position and therefore this pulse is inserted or otherwise included.

For the third pulse of the base frequency signal, the third digit of the binary carry sequence is 0 and therefore this pulse is included.

For the fourth pulse of the base frequency signal, n=4 and the fourth digit of the binary carry sequence is 2. The binary number 110101 has a "0" at the 3rd position and therefore this pulse is suppressed or otherwise omitted.

This can be continued until 63 pulses have issued. The 64$^{th}$ pulse (or, generally, the last pulse in the sequence) should be retained by convention, after which n is reset at one and the sequence repeats. Thus, for power level 53 (110101), pulses are included corresponding to points where the binary carry sequence has a 0, 1, 3 or 5 and omitted where it has a 2 or 4. For power level 39 (binary 100111), pulses are included at points where the binary carry sequence has a 0, 3, 4 or 5 and omitted where it has a 1 or 2. It will be seen that this corresponds to the illustration in FIG. 4.

If, for some reason, it was desired to provide only 50 power levels then the pattern appropriate to the next higher power of 2 (i.e., 64) could be adopted and then some power levels omitted. These would best be omitted in any areas where less sensitivity is needed; for example, if the treatment planning apparatus needed greatest sensitivity near the maximum and minimum power levels, then power levels 33, 35, 37 . . . and 31, 29, 27 . . . could be omitted. Alternatively, if it was found that the treatment planning apparatus never called for the very low power outputs then levels 1 to 15 could be omitted.

Figure 5:
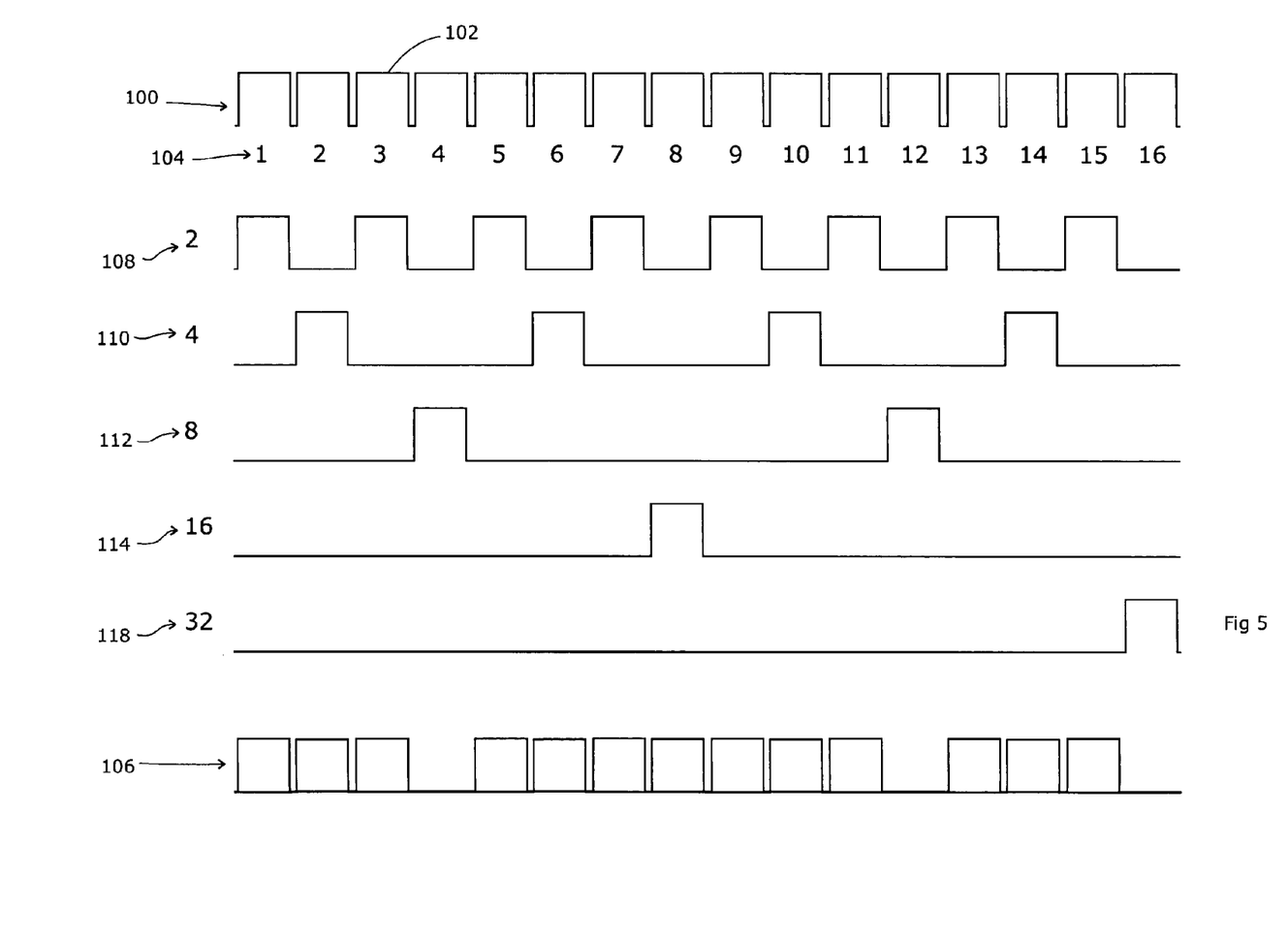
FIG. 5 shows the combination of pulse patterns to create an output.

FIG. 5 shows a further approach to generating a suitable pulse pattern. Line 100 shows the base frequency, and each pulse 102 is numbered at 104 for clarity. The pulses are shown with a very much larger mark-space ratio than would be the case in order to make clear where a pulse has been omitted.

The desired pulse pattern 106 is, in this example, a composite of several individual pulse patterns 108, 110, 112, 114, 118. A total of five individual pulse patterns are shown, in order to allow a resolution of $\frac{1}{32}^{nd}$, but the pattern is readily extendable to give a higher resolution.

Pulse pattern 108 includes every second pulse and starts with the first pulse 1. Thus, it includes pulses 1, 3, 5, 7, 9, 11, 13, 15 etc. Pulse pattern 110 includes every fourth pulse, starting with the first pulse 2 that is omitted from pulse pattern 108. Thus, it includes pulses 2, 6, 10, 14, etc. Pulse pattern 112 includes every eighth pulse and starts with the first pulse 4 omitted from both pulse pattern 108 and pulse pattern 110, i.e. pulses 4, 12, 20 (not shown) etc. Pulse pattern 114 includes every sixteenth pulse and starts with the first pulse 8 that is not present in any of pulse patterns 108, 110 and 112. Thus, it includes pulses 8, 24 (not shown), 40 (not shown) etc. Finally, pulse pattern 118 includes every thirty-second pulse and starts with the first pulse 16 that is not present in any of pulse patterns 108, 110, 112 and 114, i.e. pulses 16, 48 (not shown) etc.

In general, each pulse pattern has a frequency that is $\frac{1}{2}^k$th that of the base frequency and is offset from a pulse of the base frequency by $2^{(k-1)}$ pulses. In the example shown, the patterns are offset from the $0^{th}$ pulse (not shown) of the base frequency, but in practice what matters of course is the relative offset between the various patterns. In these expressions, k is an integer and is different for each signal. Ideally, there is a pattern for each value of of k between 1 and its upper limit in the particular instance—in this case 5, but ideally between 6 and 10.

Thus, the kth pulse pattern includes every $2^k$th pulse of the base frequency signal, and will be timed so that its pulses fall into a position that is not co-incident with a pulse in any of the $1^{st}$ to (k−1)th pulse patterns.

To create the pulse pattern for (for example) a power level that is $\frac{13}{16}$ of the maximum output power, we select the patterns containing every $2^{nd}$, $4^{th}$ and $16^{th}$ pulses (since $\frac{1}{2}+\frac{1}{4}+\frac{1}{16}=\frac{13}{16}$) and produce a pulse pattern that is a composite of them all. This is readily done in practice by suppressing (such as by switching off or otherwise deactivating, disconnecting or ignoring) all other pulse patterns and combining the required pulse patterns via an OR operation. The result is the line shown at 106 which is a pattern of the type described above. That signal can then be used to trigger pulses of the therapeutic beam.

Other resolutions could be obtained in a corresponding manner, by using more or fewer signals constructed in a corresponding manner.

These give, in practice, a pattern identical to that shown in FIG. 4. The choice between the different approaches is therefore one of engineering and/or programming convenience.

A further alternative approach to the invention is to generate the pattern of allowed and non-allowed pulses through code. A example of a straightforward program in Matlab™ scripting language able to produce the pattern to a desired modulo would be:

```
clear
bits = 4;
modulo = 2^bits;
for d = 0:(modulo−1)
    [f,e]=log2(max(d));
    binaryfield=rem(floor(d*pow2(1−max(bits,e):0)),2);
    for i = 1:bits
        shift = (2^(i−1));
        cycle = 2^i;
        j = 1;
        position(j,i) = shift;
        while position(j,i) < modulo
            position(j+1,i) = position(j,i) + cycle;
            j = j + 1;
        end
    end
    for i = 1:bits
        position(:,i) = position(:,i)*binaryfield(:,i);
    end
    for i = 1:modulo
        if (isempty(find(position == i)))
            bitstream(i) = 0;
        else
            bitstream(i) = 1;
        end
    end
    table(d+1,:) = bitstream;
end
```

Figure 6:
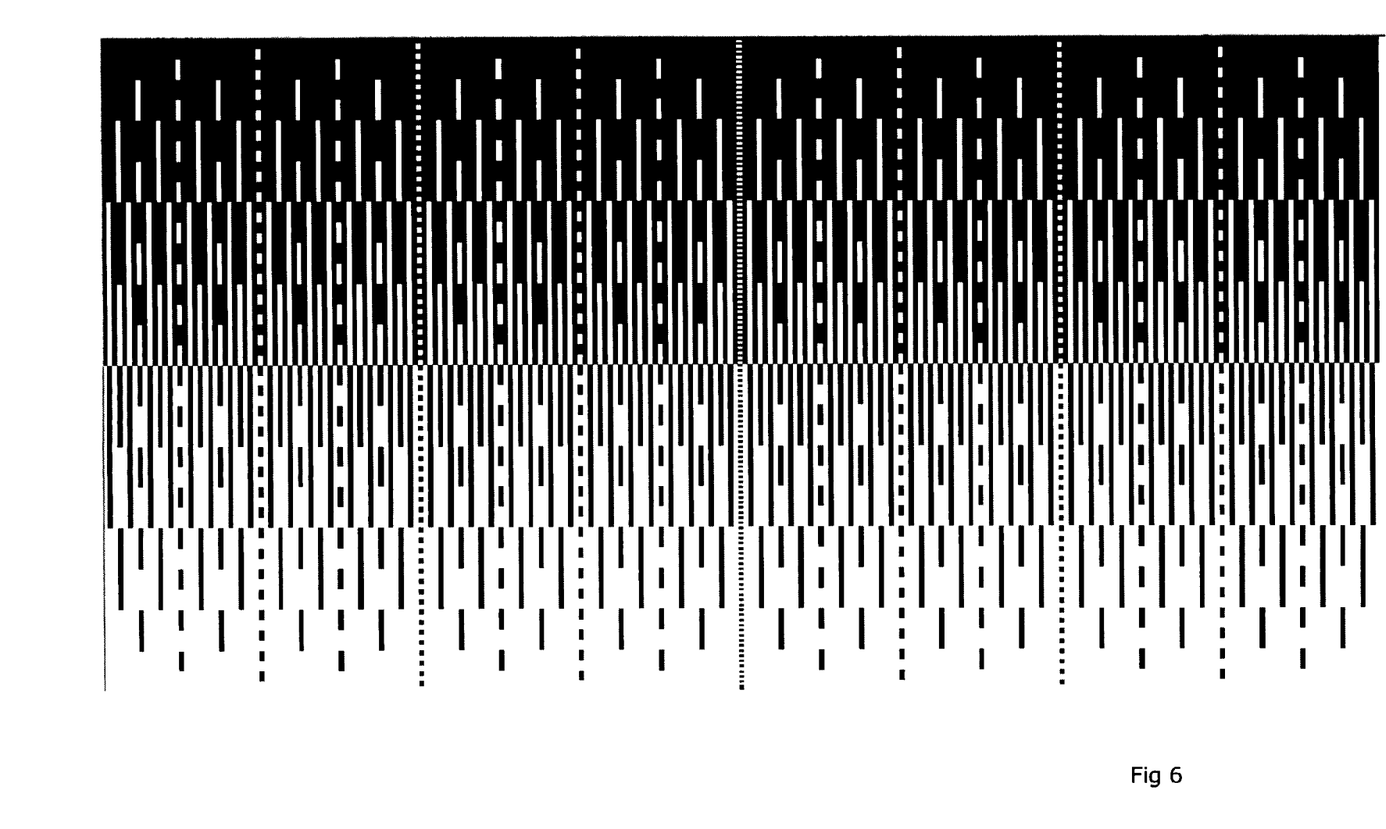
FIG. 6 shows a pulsed output modulo 256.

We propose that, in practice, a modulo 256 pattern should be used as shown in FIG. 6. This choice is arbitrary and could be larger or smaller. It does however allow the correct dose rate granularity to be achieved, essentially 256 unique dose rates. In principle, any number could be selected; a higher number will offer finer control of the power output, but this may not be necessary in practice.

The range of useful pattern sizes is dictated by the relationship between the modulo and base frequency. A modulo 256 pattern used on apparatus with a 400 Hz base frequency will repeat every $256/400$ seconds, i.e. 0.64 seconds. A modulo 4096 pattern would repeat every $4096/400$ seconds, i.e. slightly over 10 seconds. In practice, this is of little use for techniques such as VMAT, in which it is unlikely that the apparatus will be operating at a constant dose rate for over 10 seconds. A modulo 256 pattern is therefore a compromise, which approximates to a continuous adjustment with a degree of granularity that is small enough to be of little or no concern. In practice, a modulo of between $2^6$ and $2^{10}$ is likely to offer a useful compromise.

It will of course be understood that many variations may be made to the above-described embodiment without departing from the scope of the present invention.

The invention claimed is:

1. Radiotherapeutic apparatus comprising:
   a source of radiation able to issue pulses of radiation at a base frequency, and
   a control apparatus arranged to permit pulses according to a pulse pattern chosen to achieve a selected time-averaged power level, the chosen pulse pattern being one selected from a plurality of pulse patterns, the plurality of pulse patterns including at least one pulse pattern consisting of a train of pulses that includes, relative to the base frequency, at least every $n^{th}$ and every $m^{th}$ pulse where n≠m and the $n^{th}$ and $m^{th}$ pulses are non-coincident.

2. Radiotherapeutic apparatus according to claim 1, in which n is a power of 2.

3. Radiotherapeutic apparatus according to claim 1, in which m is a power of 2.

4. Radiotherapeutic apparatus according claim 1, in which the selected power level is one selected from a range of possible output power levels.

5. Radiotherapeutic apparatus comprising:
   a source of radiation able to issue pulses of radiation at a base frequency, and
   a control apparatus arranged to permit pulses according to a pulse pattern, the pulse pattern being obtained by:
   i. selecting an integer representing a desired power level,
   ii. representing the integer as a binary number with leading zeros as necessary thereby to include a preset number of digits, and
   iii. permitting the $n^{th}$ pulse of the base frequency if the representation of the integer has a 1 digit at the $(q+1)^{th}$ position from left to right, where q is the digit of the binary carry sequence appearing at the (n modulo w)$^{th}$ position, where w is a further integer number greater than the integer representing the desired power level.

6. Radiotherapeutic apparatus according to claim 5, in which the desired power level is one selected from a range of w possible output power levels.

7. Radiotherapeutic apparatus according to claim 5, in which there are $2^i$ possible output power levels, where i is an integer.

8. Radiotherapeutic apparatus according to claim 7, in which i is at least 6.

9. Radiotherapeutic apparatus according to claim 7, in which i is not more than 10.

10. Radiotherapeutic apparatus according to claim 5, wherein the control apparatus comprises a generator for generating a plurality of signals at frequencies below that of the base frequency and an OR operator, each of the plurality of signals is independently selected, and the OR operator combining the selected signals.

11. Radiotherapeutic apparatus according to claim 10, wherein the plurality of signals have frequencies that are $/1;2^k$th of the base frequency, where k is an integer and is different for each signal of the plurality of signals.

12. Radiotherapeutic apparatus according to claim 11, in which the pulses of each signal are offset from a pulse of the base frequency by $2^{(k-1)}$pulses.

13. Radiotherapeutic apparatus according claim 5, in which the control apparatus comprises a memory in which a table is retained, the table containing a sequence of pulses to be issued.

14. Radiotherapeutic apparatus according to claim 13, the control apparatus adapted to compute a sequence and load this into the table when an integer representing a desired power level is selected.

15. Radiotherapeutic apparatus according to claim 13, in which the table contains sequences for a plurality of power levels and the control apparatus is adapted to select a desired sequence.

16. Radiotherapeutic apparatus comprising:
a source of radiation able to issue pulses of radiation at a base frequency, and
a control apparatus in which are defined a plurality of pulse patterns, each pulse pattern of the plurality of pulse patterns is independently controllable between a "suppress" state and an "active" state, and each pulse pattern of the plurality of pulse patterns controls every $n^{th}$ pulse, n being different for each pulse pattern,
wherein the control apparatus is arranged to suppress a pulse if
i. a pulse pattern in a "suppress" state controls that pulse, and
ii. that pulse is not controlled by a pulse pattern with a higher value of n that is in an "active" state.

17. Radiotherapeutic apparatus according to claim 16, in which the available values of n are $n=2^p$ where p is a positive integer.

18. Radiotherapeutic apparatus according to claim 17, in which p is at least 6.

19. Radiotherapeutic apparatus according to claim 17, in which p is not more than 10.

20. Radiotherapeutic apparatus comprising:
a source of radiation able to issue pulses of radiation at a base frequency, and
a control apparatus arranged to permit pulses according to a pulse pattern obtained by selecting an integer representing a desired power level, and then inserting an $n^{th}$ pulse if the binary number representing the integer has a 1 digit at the $(q+1)^{th}$ position from left to right, where q is the nth digit of the binary carry sequence.

* * * * *

UNITED STATES PATENT AND TRADEMARK OFFICE
CERTIFICATE OF CORRECTION

PATENT NO.       : 8,995,617 B2             Page 1 of 1
APPLICATION NO.  : 13/503478
DATED            : March 31, 2015
INVENTOR(S)      : Kevin Brown et al.

It is certified that error appears in the above-identified patent and that said Letters Patent is hereby corrected as shown below:

In the Claims

In Col. 10, line 51
replace "/1;$2^k$th"
with -- $1/2^k$th --

Signed and Sealed this
Fourteenth Day of July, 2015

Michelle K. Lee
*Director of the United States Patent and Trademark Office*